(12) United States Patent
Morita

(10) Patent No.: US 11,065,159 B2
(45) Date of Patent: Jul. 20, 2021

(54) ABSORBENT ARTICLE

(71) Applicant: DAIO PAPER CORPORATION, Ehime (JP)

(72) Inventor: Tomotaka Morita, Tochigi (JP)

(73) Assignee: DAIO PAPER CORPORATION, Ehime (JP)

(*) Notice: Subject to any disclaimer, the term of this patent is extended or adjusted under 35 U.S.C. 154(b) by 323 days.

(21) Appl. No.: 16/080,431

(22) PCT Filed: Feb. 24, 2017

(86) PCT No.: PCT/JP2017/007118
§ 371 (c)(1),
(2) Date: Aug. 28, 2018

(87) PCT Pub. No.: WO2017/150378
PCT Pub. Date: Sep. 8, 2017

(65) Prior Publication Data
US 2019/0008700 A1    Jan. 10, 2019

(30) Foreign Application Priority Data
Mar. 3, 2016  (JP) .............................. JP2016-040807

(51) Int. Cl.
*A61F 13/533*  (2006.01)
*A61F 13/537*  (2006.01)
(Continued)

(52) U.S. Cl.
CPC ........ *A61F 13/4756* (2013.01); *A61F 13/475* (2013.01); *A61F 13/5125* (2013.01);
(Continued)

(58) Field of Classification Search
CPC .............. A61F 13/4704; A61F 13/4756; A61F 13/49001; A61F 13/51104;
(Continued)

(56) References Cited

U.S. PATENT DOCUMENTS 5,891,118 A    4/1999 Toyoshima et al.
6,700,034 B1*  3/2004 Lindsay .............. A61F 13/4704
                                                604/367
(Continued)

FOREIGN PATENT DOCUMENTS

JP    H9-168563      6/1997
JP    2002-330992    11/2002
(Continued)

OTHER PUBLICATIONS

International Search Report for PCT/JP2017/007118 dated May 23, 2017.
(Continued)

*Primary Examiner* — Catharine L Anderson
(74) *Attorney, Agent, or Firm* — IPUSA, PLLC

(57) ABSTRACT

An absorbent body 4 is provided between a liquid permeable topsheet 3 and a liquid impermeable backsheet 2, and a second sheet 6 is provided between the liquid permeable topsheet 3 and the absorbent body 4. Slits 10 that penetrate in the thickness direction are formed along a longitudinal direction on both sides of the absorbent body 4 in the width direction, a body fluid expelling portion corresponding region H is included between the slits, the second sheet 6 is provided along an inner surface of the slits, and concave grooves 11, in which the second sheet 6 and the liquid impermeable backsheet 2 are integrated, are formed in the slits. At least a portion of the second sheet 6 constituting one of the side surfaces of the concave groove 11 has water-repellent properties.

7 Claims, 9 Drawing Sheets

(51) Int. Cl.
*A61F 13/475* (2006.01)
*A61F 13/532* (2006.01)
*A61F 13/539* (2006.01)
*A61F 13/512* (2006.01)

(52) U.S. Cl.
CPC .......... *A61F 13/532* (2013.01); *A61F 13/533* (2013.01); *A61F 13/537* (2013.01); *A61F 13/539* (2013.01); *A61F 13/53704* (2013.01)

(58) Field of Classification Search
CPC .............. A61F 13/51108; A61F 13/532; A61F 13/533; A61F 13/536; A61F 13/537; A61F 13/53704; A61F 13/539
See application file for complete search history.

(56) References Cited

U.S. PATENT DOCUMENTS 9,220,642 B2 * 12/2015 Hayashi .............. A61F 13/4702
9,789,011 B2 * 10/2017 Roe .................... A61F 13/5125
2011/0172630 A1 * 7/2011 Nomoto .............. A61F 13/4756
  604/385.201
2013/0226123 A1 * 8/2013 Kudo .................... A61F 13/538
  604/380
2016/0213525 A1 7/2016 Suzuki et al.

FOREIGN PATENT DOCUMENTS

| JP | 2007-215913 | 8/2007 |
| JP | 2013-172813 | 9/2013 |
| JP | 2015-44046 | 3/2015 |
| JP | 2015-47432 | 3/2015 |
| WO | 2001/024752 | 4/2001 |

OTHER PUBLICATIONS

Extended European search report for European Patent Application No. 17759844.8 dated Feb. 18, 2019.

* cited by examiner (A)

(B)

(A)

(B)

US 11,065,159 B2

ABSORBENT ARTICLE

BACKGROUND OF THE INVENTION

1. Field of the Invention

The present invention relates to an absorbent article.

2. Description of the Related Art

Conventionally, as absorbent articles such as panty liners, sanitary napkins, and incontinence pads, a structure is known that has an absorbent body made of cotton-like pulp between a liquid impermeable backsheet such as a polyethylene sheet or a polyethylene-sheet-laminated non-woven fabric and a liquid permeable topsheet such as a non-woven fabric or a liquid permeable plastic sheet.

Such types of absorbent articles are practically formed in a vertically-long shape, and, in particular, have wing-shaped flaps that are folded back so as to wrap around the crotch portion of an undergarment and are fixed to an outer surface of the crotch portion of the undergarment when it is worn. Further, in a what is termed as nighttime sanitary napkin that has hip-hold flaps formed on the rear side of the wing-shaped flaps and used for preventing the absorbent article from shifting in a lateral direction and for preventing a leakage of body fluids, the longitudinal size is longer than the width size in order to cover a wide range from the front side to the buttock side of the crotch portion of a wearer. Therefore, there has been a problem of an occurrence of a leakage in the width direction with shorter size in spite of the fact that there is enough room for absorbing fluids in the longitudinal direction. In other words, when body fluids absorbed in the absorbent body is diffused inside the absorbent body, the body fluids readily reach edges (side edges) in the width direction whose size is shorter than the size in the longitudinal direction, and thus, a lateral leakage, in which the body fluids leak to the outside from the side edges of the absorbent body, readily occurs.

As a technique for preventing this kind of lateral leakage, in Patent Document 1, an absorbent article is described in which: leakage-preventing sheets are provided (disposed) on both sides (left and right sides) of the surface of the absorbent article so as to form a pair of hydrophobic areas (non-absorbent areas) from side edges towards inner sides; and the hydrophobic areas include continuous or non-continuous leakage-preventing grooves that are formed along the longitudinal direction in the absorbent article.

Further, in Patent Document 2, an absorbent article is described in which: a water-repellent side sheet is joined to each of both sides of the surface sheet in the longitudinal direction; the side sheet is provided to cover at least from the skin contacting surface of the absorbent body to the side surface in a section view along the width direction; and a double leakage-preventing structure is formed by the side sheet and a leakage-preventing wall in an expelling-portion facing portion that is provided to face a fluid expelling portion of a wearer when it is worn.

CITATION LIST

Patent Document

[Patent Document 1] Japanese Unexamined Patent Application Publication No. H9-168563

[Patent Document 2] Japanese Unexamined Patent Application Publication No. 2007-215913

SUMMARY OF THE INVENTION

Technical Problem

In absorbent articles described in Patent Document 1 and Patent Document 2, it is possible to prevent body fluid leakages from the side surface of the absorbent body by providing a leakage-preventing sheet or a water-repellent side sheet so as to wrap around the side edge of the absorbent body from the rear surface side to the front surface side. However, because the body fluids absorbed in the absorbent body are diffused inside and reach the side edges of the absorbent body, there is a case in which, when a wearer sees how body fluids are diffused after use, even if there is no actual lateral leakage, visually, the wearer feels concerned that the lateral leakage might have almost occurred.

Further, in an absorbent article described in Patent Document 1, the leakage-preventing sheet is formed by having a back sheet folded back to the front surface side so as to wrap around the side surface of the absorbent body, and the back sheet, which consists of a plastic sheet or the like and generally has high rigidity, is extended to the front surface side, and thus, there is a risk of degrading the wearing comfort. Furthermore, after producing a sanitary napkin without groove, leakage-preventing grooves are formed by embossing roll or the like, by compressing the front surface sheet, the leakage-preventing sheet, and the absorbent body together from the front surface side along the longitudinal direction of the sanitary napkin. As a result, a joined portion, in which the absorbent body, the front surface sheet, and the leakage-preventing sheet are joined together at the groove portion, tends to come off due to twists of the absorbent article that are generated when it is worn, and thus, there is a risk of degrading the wearing comfort and decreasing the body fluid leakage-preventing effects. Further, in Patent Document 2, a water-repellent side sheet is joined to each of the side portions of the surface sheet in the longitudinal direction. However, there is a problem that the joined portion, in which the front surface sheet and the side sheet are joined to each other, comes off due the twists of the absorbent article, and there is a problem that the lateral-leakage-preventing effects of the side sheet is decreased in the case where a crepe paper sheet, which surrounds the absorbent body and has become easy to tear due to the body fluid absorption, is teared due to, for example, the twists of the absorbent article.

Therefore, the principal purpose of the present invention is to provide an absorbent article that reliably prevents the lateral leakage, that visually prevents an occurrence of a concern about the lateral leakage, and that increases the wearing comfort.

Solution to Problem

According to an aspect, an absorbent article is provided. In the absorbent article, an absorbent body is provided between a liquid permeable topsheet and a backsheet, and a second sheet is provided between the liquid permeable topsheet and the absorbent body. Slits that penetrate in the thickness direction are formed along the longitudinal direction on both side portions of the absorbent body in the width direction, a body-fluid-expelling-portion corresponding region is included between the slits, the second sheet is provided along an inner surface of the slits, concave grooves, in which the second sheet and the backsheet are integrated, are formed in the slits, and at least a portion of the second sheet that forms one of the side surfaces of the concave grooves has water-repellent properties.

Advantageous Effects of Invention

According to an embodiment of the present invention, it is possible to reliably prevent the lateral leakage, to visually prevent an occurrence of a concern about the lateral leakage, and to increase the wearing comfort.

DETAILED DESCRIPTION OF THE PREFERRED EMBODIMENTS

In the following, one or more embodiments of the present invention will be described while making reference to the drawings.

Absorbent articles may be a sanitary napkin, a panty liner, an incontinence pad, a toiletry (personal care article), etc. In an embodiment of the present invention, an absorbent article has a structure for preventing body fluid diffusion, used for preventing diffusion of body fluids on both sides of the body-fluid-expelling-portion corresponding region. A case, in which the absorbent article is a sanitary napkin, will be described below as an example.

[Basic Structure of Sanitary Napkin 1]

Figure 1:
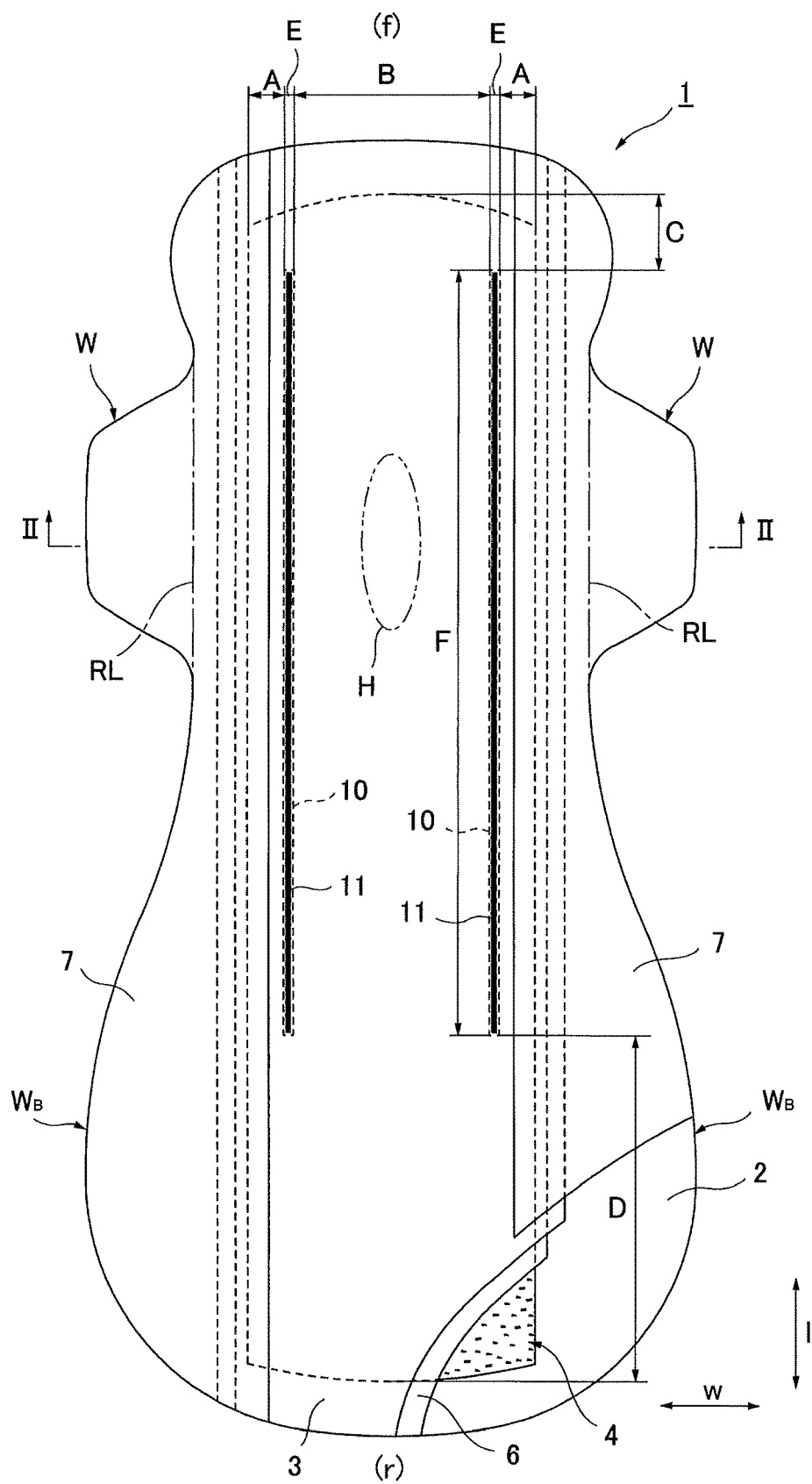
FIG. 1 is a partially broken development view of a sanitary napkin according to an embodiment of the present invention.
Figure 2:
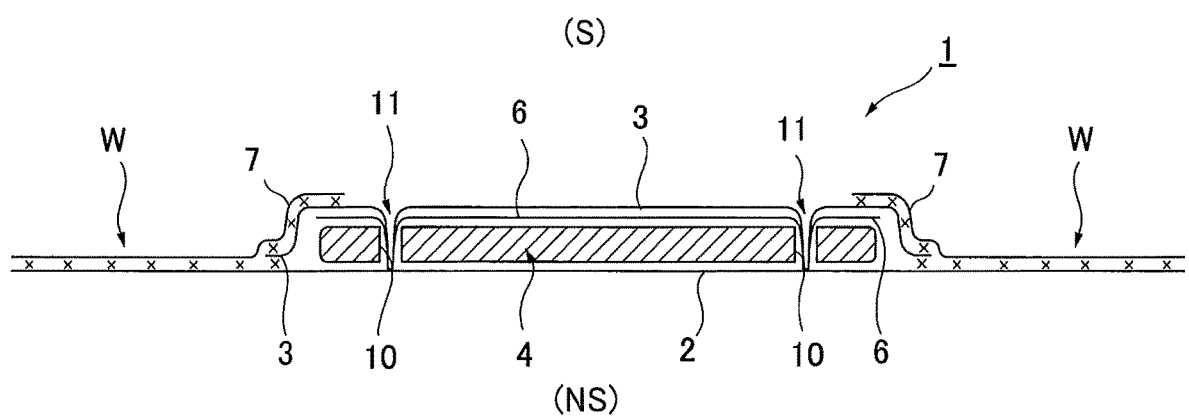
FIG. 2 is a cross-sectional view taken along a line II-II of FIG. 1.
Figure 3:
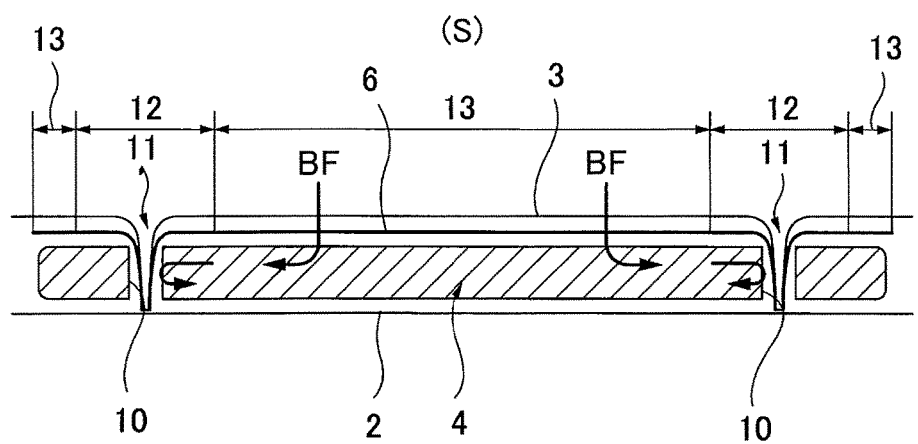
FIG. 3 is a cross-sectional view of a sanitary napkin in which a diffusion state of body fluids is indicated.

FIG. 1 is a partially broken development view of a sanitary napkin 1 according to an embodiment of the present invention. FIG. 2 is a cross-sectional view taken along a line II-II of FIG. 1. FIG. 3 is a cross-sectional view of a sanitary napkin 1 in which a diffusion state of body fluids is indicated. It should be noted that, in FIG. 1, the front side is indicated by "f", the rear side is indicated by "r", the width direction is indicated by "w", and the longitudinal direction is indicated by "l".

As illustrated in FIG. 1 and FIG. 2, the sanitary napkin 1 includes a liquid impermeable backsheet 2, a liquid permeable topsheet 3, an absorbent body 4 that is provided between the backsheet 2 and the topsheet 3, side non-woven fabric sheets 7, and a second sheet 6. The liquid impermeable backsheet 2 is made of a polyethylene sheet or the like. The liquid permeable topsheet 3 allows menstrual blood, vaginal discharge, and the like (which are hereinafter referred to as body fluids) to quickly pass through. The absorbent body 4 is made of pulp, such as cotton-like pulp or synthetic pulp. The side non-woven fabric sheets 7 are provided on both lateral sides of the skin contact surface side and along the longitudinal direction covering almost the entire longitudinal length. The second sheet 6 is provided between the liquid permeable topsheet 3 and the absorbent body 4. Around the absorbent body 4, peripheral portions of the liquid impermeable backsheet 2 and the liquid permeable topsheet 3 are joined to each other by bonding means such as adhesive agent like a hot melt, a heat seal, and an ultrasonic sound wave seal at the periphery of a top end and a lower end of the absorbent body 4. Furthermore, on both peripheries of the absorbent body 4, the liquid impermeable backsheet 2 and the side non-woven fabric sheets 7 that laterally extend longer than the absorbent body 4 are joined to each other by an adhesive agent such as hot melt, heat seal, supersonic sound wave seal and the like. Stacked sheet parts of the liquid impermeable backsheet 2 and the side non-woven fabric sheets 7 form wing-shaped flaps W, W that protrude laterally up to a location outside the absorbent body 4. Moreover, hip-hold flaps $W_B$, $W_B$ are formed on portions located on the buttock side of the wing-shaped flaps W, W. The sanitary napkin 1 may be what is termed as a nighttime napkin that covers a wide range of the buttock of the wearer and extends long backward. An encapsulating sheet (not shown) that surrounds the absorbent body 4 and is made of crepe paper, non-woven fabric or the like may be included in order to retain the shape of the absorbent body 4 and to enhance diffusivity of the absorbent body 4.

Furthermore, the structure of the sanitary napkin 1 will be described in detail below.

As the liquid impermeable backsheet 2, a sheet material made of polyethylene, or the like, having at least a water interception property is used. It is desirable that a material having moisture permeability is used in order to prevent dampness. As this water shielding and permeable sheet material, a microporous sheet, which is obtained by stretching it in one axial direction or two axial directions after forming a sheet by melting and kneading an inorganic filler in olefin resin such as polyethylene and polypropylene, is preferably used. On a non-skin side surface (an outer surface, indicated by "NS" in the figure), one or more lines of adhesive layers (not shown) are formed along the longitudinal direction of the napkin, which are used for fixing the sanitary napkin 1 to the undergarment when wearing it on the body. As the liquid impermeable backsheet 2, a polyethylene-laminated non-woven fabric, in which a plastic film and a non-woven fabric are stacked, may be used.

Next, as the liquid permeable topsheet 3, a perforated or imperforate non-woven fabric or a porous plastic sheet is preferably used. As a material for constituting the non-woven fabric, in addition to a synthetic fiber including an olefin series such as polyethylene or polypropylene, a polyester series, a polyamide series and the like, a regenerated fiber such as rayon or cupra (cuprammonium rayon), a natural fiber such as cotton may be used, and a non-woven fabric obtained by an appropriate processing method such as a spun lace method, a spun bond method, a thermal bond method, a melt blown method or a needle punch method may be used. Among these processing methods, the spun lace method is superior in terms of great flexibility and drape properties, and the thermal bond method is superior in terms of bulkiness and compression restorability. When a plurality of through holes are formed in the liquid permeable topsheet 3, the body fluids can be rapidly absorbed and a dray touch property becomes good. A fiber of the non-woven fabric may be either one of a long fiber and a short fiber. However, the short fiber is preferably used to show texture of toweling. Further, an olefin-base fiber such as polyethylene or polypropylene having a relatively low melting point is preferably used to make it easy to apply an embossing process. Further, a composite fiber such as a core/sheath type fiber in which a fiber having a high melting point is used as a core and a fiber having a low melting point is used as a sheath, a side-by-side type fiber, a divided type fiber or the like may be preferably used.

The absorbent body 4 provided between the liquid impermeable backsheet 2 and the liquid permeable topsheet 3 is, for example, constituted of cotton-like pulp and absorbent polymer. The absorbent polymer is mixed into the pulp constituting the absorbent body as granular powders, for example. As the pulp, chemical pulp obtained from wood, a cellulose fiber such as dissolving pulp, and an artificial cellulose fiber such as rayon or acetate may be listed, and softwood pulp having a fiber length longer than that of hardwood pulp is preferably used in terms of function and price.

Further, a synthetic fiber may be mixed into the absorbent body 4. The synthetic fiber may be, for example, a polyolefin series such as polyethylene or polypropylene, a polyester series such as polyethylene terephthalate or polybutylene terephthalate, a polyamide series such as nylon, a copolymer thereof, or a mixture of two kinds thereof. Furthermore, a composite fiber such as a core-clad type fiber including a core made of a fiber with a high melting point and a clad made of a fiber with a low melting point, a side-by-side type fiber or a division type fiber may also be used. When the synthetic fiber is made of a hydrophobic fiber, it is preferable to treat a surface of the synthetic fiber with a hydrophilic agent so that the synthetic fiber has hydrophilic properties to the body fluids.

As illustrated in FIG. 2, a second sheet 6 is provided between the liquid permeable topsheet 3 and the absorbent body 4. The second sheet 6 will be described in detail in the following stage.

As illustrated in the lateral cross-sectional view of FIG. 2, a width size of the liquid permeable topsheet 3 is slightly longer than a width of the absorbent body 4 to cover only the absorbent body 4. The side non-woven fabric sheets 7 that are different from the liquid permeable topsheet 3 are provided on the outer sides of the absorbent body 4. The side non-woven fabric sheets 7 are made of a non-woven fabric material on which an appropriate water-repellent treatment or hydrophilic process is performed specifically depending on a desired function such as a function of preventing menstrual blood or vaginal discharge from permeating or of improving a texture. As such non-woven fabric sheets 7, non-woven fabric sheets, which are formed by applying an appropriate processing method on a material such as a natural fiber, a synthetic fiber or a regenerated fiber, may be used, and preferably, non-woven fabrics, whose basis weight is reduced to have air permeability, may be used for eliminating hardness and prevent sweating. Specifically, it is desirable to use non-woven fabrics manufactured to have a basis weight of 13 to 23 $g/m^2$, and it is preferable to use water-repellent non-woven fabrics on which a water-repellent agent of a silicon series, a paraffin series or an alkyl chromic chloride series is coated for reliably preventing the permeating of the body fluids.

As illustrated in FIG. 2, regarding the side non-woven fabric sheet 7, an outer side portion from an intermediate portion in the width direction is adhered to, by adhesive agent like a hot melt, an area ranging from the inside position of the absorbent body 4, slightly exceeding the side edge of the absorbent body 4, to the outer edge of the liquid impermeable backsheet 2. A pair of wing-shaped flaps W, W in the lateral direction are formed at side positions of the absorbent body almost corresponding to the body fluid expelling portion, and, as illustrated in FIG. 1, hip-hold flaps $W_B$, $W_B$ are formed at further buttock side (rear side) positions, by the stacked sheet portions of the side non-woven fabric sheets 7 and the liquid impermeable backsheet 2. An adhesive layer (not shown) is provided at an outer surface side of each of these wind-shaped flaps W, W, and the hip-hold flaps $W_B$, $W_B$, and when attached to the panties, the wing-shaped flaps W, W are each bent at positions of folding lines RL towards the opposite sides to be wrapped around the crotch portion of the panties to be fixed, and the hip-hold flaps $W_B$, $W_B$, are fixed to the inner surface of the panties. On the other hand, as illustrated in FIG. 2, inner sides of the side non-woven fabric sheets 7 cover only side edge portions of the absorbent body 4, and are adhered to the liquid permeable topsheets 3 by adhesive agent like a hot melt.

[Regarding Concave Grooves]

In order to reliably prevent the lateral leakage, and to visually prevent an occurrence of a concern about the lateral leakage, a sanitary napkin 1 according to an embodiment of the present invention includes concave grooves for suppressing the body fluid diffusion in the absorbent body 4. The concave grooves will be described in detail below.

As illustrated in FIG. 1 to FIG. 3, in a sanitary napkin 1 according to an embodiment of the present invention, slits 10, 10, which penetrates in the thickness direction, are each formed along the longitudinal direction on both sides of an area including a body-fluid-expelling-portion corresponding area H of the absorbent body 4. The slits 10, which are provided as a pair on both sides at intermediate positions in the width direction of the absorbent body 4, are penetrating portions of the absorbent body in which pulp or polymer, of which the absorbent body 4 is made, does not exist. "Material, of which the absorbent body 4 is made, does not exist in the slits 10" means that the material does not exist at all, or, that the material exists in a very small amount due to, for example, spilled granular powders of polymer during the manufacturing process but the amount is extremely small compared with the surroundings.

Further, as illustrated in the lateral cross-sectional views of FIG. 2 and FIG. 3, in a sanitary napkin 1 according to an embodiment of the present invention, at least a second sheet 6 provided on the skin side surface of the absorbent body 4 (indicated by "S" in the figure) is provided along the inner surface of the slits 10, and concave grooves 11, in which at least the second sheet 6 and the liquid impermeable backsheet 2 are integrated, are formed in the slits 10.

In the second sheet 6, at least a portion, which is included in one of the side surfaces of the concave groove 11, is a water-repellent area 12 having water-repellent property. The water-repellent area 12 of the second sheet 6 is continuously formed from the bottom of the concave groove 11 towards the skin side surface of the absorbent body 4 so as to cover at least all of one of the side surfaces of the second sheet 6 by which the concave groove 11 is formed.

With the above arrangement, as illustrated in FIG. 3, the body fluids (indicated by "BF" in the figure) that diffuse inside the absorbent body 4 is blocked by the water-repellent area 12 of the second sheet 6, the diffusion of the body fluids towards the outer side beyond the slits 10 is suppressed, and the body fluids are retained in the absorbent body 4 between the slits 10, 10. Therefore, it is possible to reliably prevent the lateral leakage of the body fluids, and it is possible to cause a wearer not to be concerned about the lateral leakage because there remains a portion of the absorbent body in a pure white state in which no body fluids are diffused in the outer side of the slits 10 in the width direction when the wearer checks a diffusion state of the body fluids after use.

Figure 4:
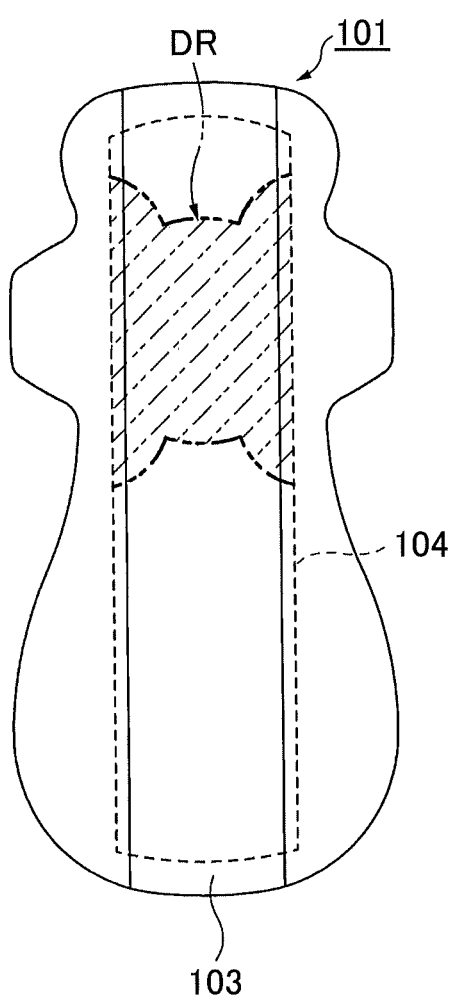
FIGS. 4(A) and (B) are planar views of (A) a conventional sanitary napkin and (B) a sanitary napkin according to an embodiment of the present invention in which diffusion states of body fluids are indicated.
Figure 4:
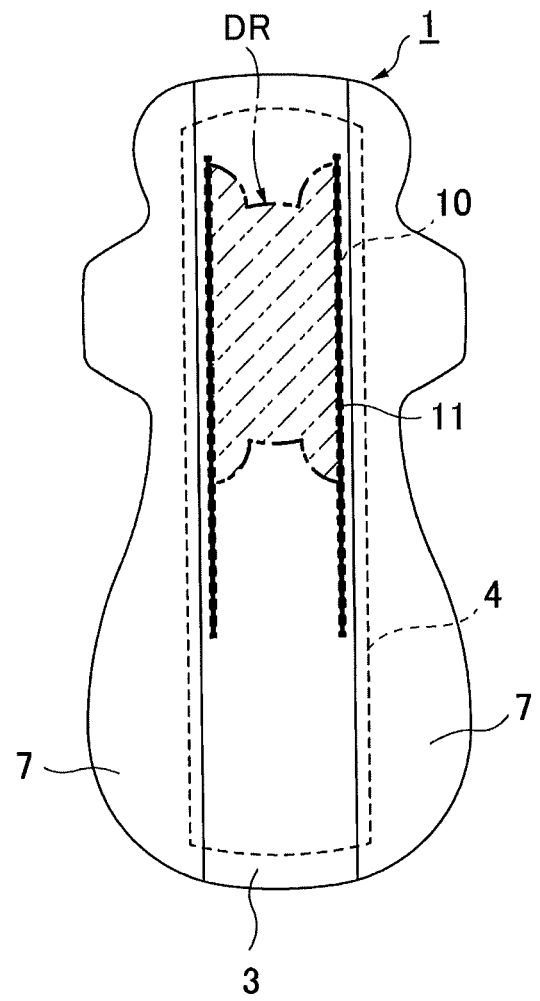

Next, referring to FIG. 4(A) and FIG. 4(B), diffusion states of the body fluids will be further described in detail. FIG. 4(A) illustrates a diffusion state of the body fluids in a conventional sanitary napkin 101. FIG. 4(B) illustrates a diffusion state of the body fluids in a sanitary napkin 1 according to an embodiment of the present invention.

As illustrated in FIG. 4(A), the conventional sanitary napkin 101 does not include the above-described concave groove 11 for suppressing the diffusion of the body fluids ("103" indicates the topsheet). In the conventional sanitary napkin 101, body fluids absorbed in an absorbent body 104 are diffused evenly in a circular range whose center is the body-fluid-expelling-portion corresponding region, and the body fluids, which have reached the edge of the absorbent body 104 in the short-length width direction and have been prevented from diffusing in the width direction, are diffused in the longitudinal direction. Therefore, the lateral leakage, in which the body fluids leak out of the side edges of the absorbent body 104, readily occurs. It should be noted that a body fluid diffusion region is indicated by "DR" in FIG. 4(A) and FIG. 4(B).

On the other hand, as illustrated in FIG. 4(B), a sanitary napkin 1 according to an embodiment of the present invention includes the above-described concave grooves 11 for suppressing the body fluid diffusion. Therefore, it is possible to prevent the lateral leakage by suppressing the diffusion of body fluids towards the outer side beyond the slits 10 in the width direction. Regarding the body fluids blocked by the slits 10, the diffusion towards the napkin's width direction is suppressed, and the direction of the diffusion is changed to the napkin's longitudinal direction. Here, the side edge portions of the absorbent body 4 are kept in white because the body fluids are not diffused towards the outer side beyond the slits 10 in the width direction. Further, because the distance at which the diffusion direction is changed to the napkin's longitudinal direction is shorter than that of the conventional napkin 101, the diffusion region expands in the longitudinal direction and a wider range of the absorbent body 4 can be used as a body fluid absorbing region.

Further, by forming the concave grooves 11, at least the second sheet 6 and the fluid impermeable backsheet 2 are integrated in the slits 10, and the absorbent body 4 does not exist in between, and thus, even if wrinkles or twists of the sanitary napkin 1 are generated when being worn, the joined portion, at which the second sheet 6 and the liquid impermeable backsheet 2 are joined to each other, won't come off, and it is possible to increase the wearing comfort and to retain effects of the body fluid leakage prevention.

The slits 10 extends almost along the napkin's longitudinal direction in a plan view. "The slits 10 extends almost along the napkin's longitudinal direction" means that the length between both ends of the slits 10 in the napkin's longitudinal direction is longer than the length of the whole slits 10 in the napkin's width direction.

Figure 10:
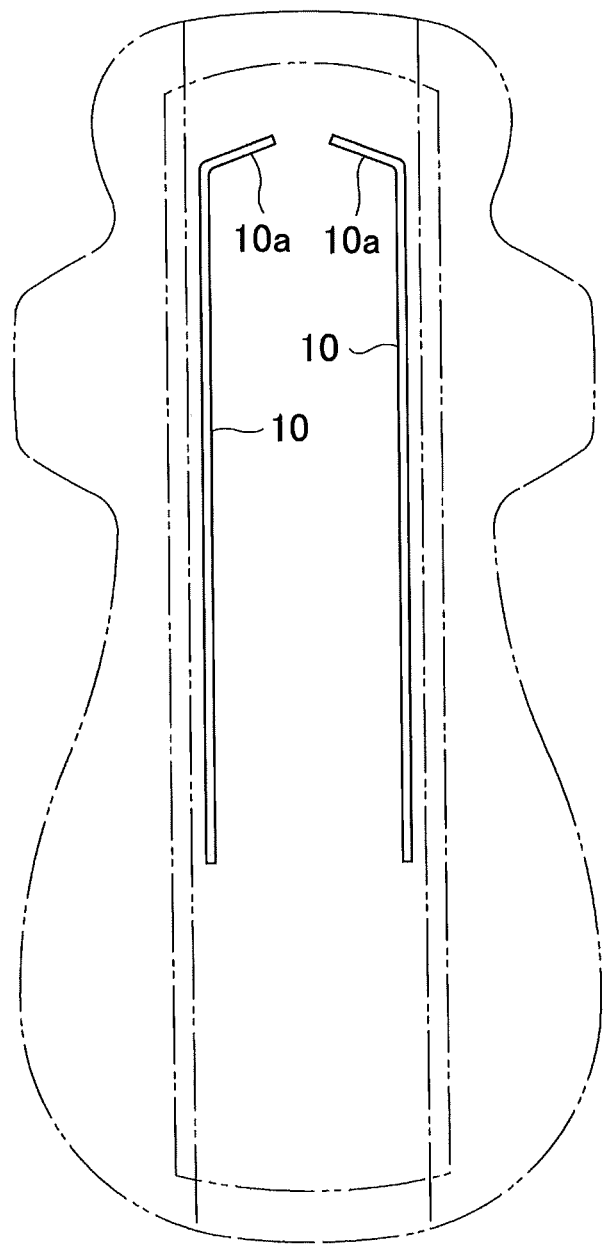
FIG. 10 is a planar view of a slit according to a modified example.
Figure 11:
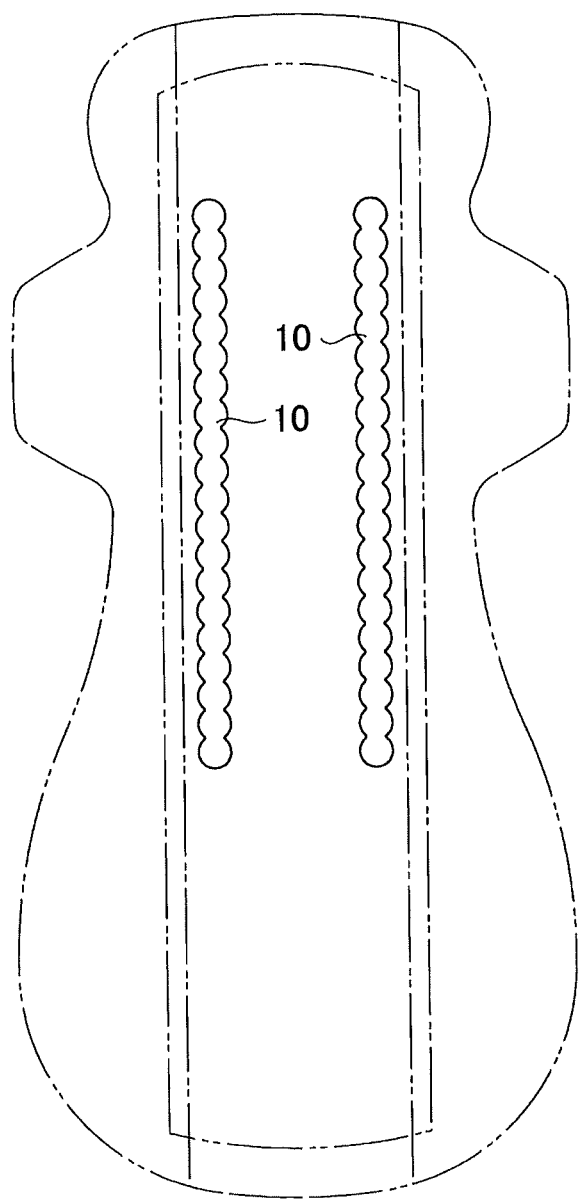
FIG. 11 is a planar view of a slit according to a modified example.

Further, the shape of the slits 10 in a plan view may be a straight line as illustrated in FIG. 1, a curve that curves towards inside or outside, a bending line, a wavy line, or a combination of two or more thereof. Further, as illustrated in FIG. 10, a bent portion 10a may be provided, in which one of or both of the front end and the rear end of the slits 10 is bent towards the inner side in the width direction. Because, in the nighttime napkin, the length of the absorbent body on the front side of the body fluid expelling portion is shorter than the length of the absorbent body on the rear side of the body fluid expelling portion, it is preferable that the bent portion 10a is provided at least at the front end of the slits 10 so as to prevent the body fluid leakage from the front side. Further, as illustrated in FIG. 11, the slits 10 may be formed in a shape of beads in which a series of circles are connected together in the longitudinal direction. With the above arrangement, wide width portions and narrow width portions are alternately formed, and the twists and wrinkles due to the leg pressure are reduced by having the narrow width portions served as a stopper.

As illustrated in FIG. 1, the positions, at which the slits 10 are provided with respect to the absorbent body 4, are intermediate positions in the napkin's longitudinal direction, and the slits 10 are formed in a range at least corresponding to the body fluid expelling portion of the wearer in the napkin's longitudinal direction. In other words, the slits 10 are formed in a range including the wing-shaped flaps W in the napkin's longitudinal direction. Further, as illustrated in an example of the figure, regarding the front side in the napkin's longitudinal direction, it is preferable that the slits 10 are formed in a range that includes the front side of the body-fluids-expelling-portion corresponding region H and that does not reach the front edge of the absorbent body 4. Further, regarding the rear side in the napkin's longitudinal direction, it is preferable that the slits 10 are formed toward a position, which is on the rear side of the body-fluids-expelling-portion corresponding region H, which does not reach the rear edge of the absorbent body 4, and at which or in the vicinity of which the width of the hip-hold flaps WB is the longest. With the above arrangement, it is possible to reliably prevent the lateral leakage of the body fluids that have been diffused to the front and the rear of the body fluid expelling site.

As illustrated in FIG. 1, regarding the specific position of the slits 10, it is preferable that a separation width A from the side edge of the absorbent body 4 is 5 to 30 mm, preferably 10 to 25 mm, in order to prevent the leakage of the body fluids and to provide good visual effects after use. Further, it is preferable that a separation width B between the slits 10, 10 on both sides is 20 to 70 mm, preferably 30 to 60 mm, in order to secure a certain amount of body fluid diffusion region in the absorbent body in the width direction. It is preferable that the slits 10 are formed: at a position coincides with the inner side edge of the side non-woven fabric sheets 7; in the vicinity thereof; or at an inner side position from the inner side edge of the side non-woven fabric sheets 7. With the above arrangement, it is possible to reliably prevent the lateral leakage of the body fluids because the body fluids, which travel on the surface of the sanitary napkin 1, are reliably drawn to and blocked by the concave grooves 11.

Further, as illustrated in FIG. 1, regarding the position of the slits 10 in the front-and-rear direction, it is preferable that a length C between the front end of the slits 10 and the front end of the absorbent body 4 in the napkin's longitudinal direction is 20 to 60 mm, preferably 30 to 50 mm. It is preferable that a length D between the rear end of the slits 10 and the rear end of the absorbent body 4 is, in the case of a sanitary napkin according to an embodiment of the present invention as a nighttime napkin, 20 to 100 mm, preferably 40 to 80 mm.

It is preferable that a width of the slits 10 is 0.5 to 5.0 mm, preferably 1.0 to 3.0 mm. It is preferable that a length of the slits is 120 to 300 mm, preferably 140 to 280 mm.

As illustrated in FIG. 2 and FIG. 3, the concave grooves 11 may be formed by applying an embossing process to the second sheet 6 and the liquid permeable topsheet 3 that are stacked on the skin side of the absorbent body 4 in which the slits 10 have been formed, from the front surface side of the liquid permeable topsheet 3 into the slits 10, causing the liquid permeable topsheet 3 and the second sheet 6 to be provided along the inner surface of the slits 10. With the above arrangement, the liquid permeable topsheet 3, the second sheet 6 and the liquid impermeable backsheet 2 are bonded by thermocompression to form an integrated structure in the slits 10, the concave grooves 11 are formed on both sides of the front surface side of the sanitary napkin 1, the body fluids traveling on the surface in the width direction are caused to flow into the concave grooves 11 to be blocked, and thus, it is possible to reliably prevent the lateral leakage.

Figure 5:
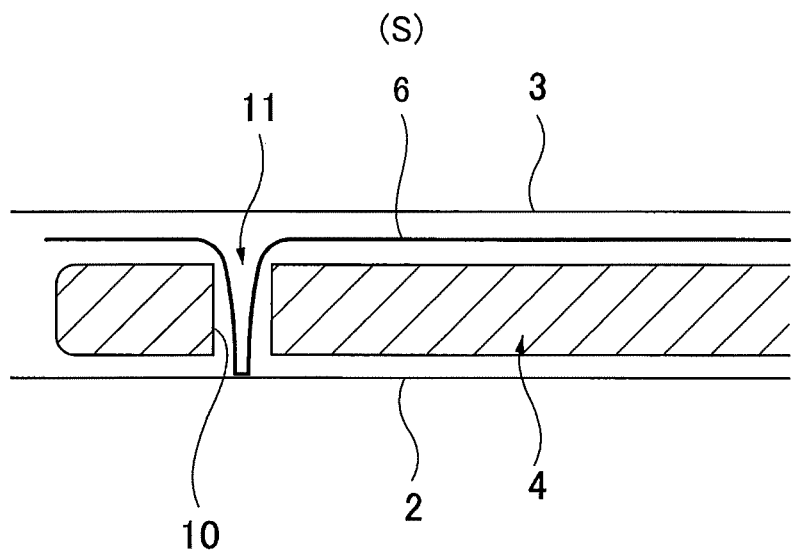
FIG. 5 is an enlarged cross-sectional view of a sanitary napkin according to a modified example.

FIG. 5 is an enlarged cross-sectional view of a sanitary napkin according to a modified example. As illustrated in FIG. 5, the concave grooves 11 may be formed by applying an embossing process to the second sheet 6 that is stacked on the skin side of the absorbent body 4 in which the slits 10 have been formed, from the front surface side of the second sheet 6 into the slits 10, causing only the second sheet 6 to be provided along the inner surface of the slits 10. With the above arrangement, the second sheet 6 and the liquid impermeable backsheet 2 are bonded by thermocompression to form an integrated structure in the slits 10, the concave grooves 11 are formed on both sides of the front surface side of the sanitary napkin 1, the body fluids traveling on the surface in the width direction are caused to flow into the concave grooves 11 to be blocked, and thus, it is possible to reliably prevent the lateral leakage.

It should be noted that, in the case where the absorbent body 4 is surrounded by an encapsulating sheet, in the bottom surface of the concave grooves 11, between the second sheet 6 and the liquid impermeable backsheet 2, there exits the encapsulating sheet that covers the front surface and the back surface of the absorbent body 4.

The embossing process for forming the concave grooves 11 is applied with respect to the slits 10 of the absorbent body 4. In other words, with the embossing process for forming the concave grooves 11, it is the second sheet 6 that is compressed, and the absorbent body 4 is not directly compressed. In short, with the embossing process for forming the concave grooves 11, an embossing convex part whose bottom surface is smaller than the slits 10 is used to form an embossed result in the slits 10. It is preferable that, regarding the size of the bottom surface of the concave grooves 11, the width is 0.5 to 3.0 mm, preferably 1.0 to 2.0 mm, and the length is 120 to 300 mm, preferably 140 to 280 mm.

By forming the concave grooves 11, as illustrated in the lateral cross-sectional view of FIG. 3, the end surfaces of the absorbent body 4 (side surfaces of the slits 10) divided at the slits 10 in the width direction are each covered by at least the second sheet 6, and at least the second sheet 6 and the liquid impermeable backsheet 2 are joined to each other in the bottom surface of the concave grooves 11.

As the second sheet 6, any one of a sheet having a hydrophilic property for the body fluids and a sheet having a water-repellent property may be used. Specifically, a material with hydrophilic property may be used by using a regenerated fiber such as rayon or cupra (cuprammonium rayon) or a natural fiber such as cotton; or a material with water-repellent property may be used by using a synthetic fiber including an olefin series such as polyethylene or polypropylene, a polyester series, a polyamide series and the like. Further, as will be described in detail in the following stage, it is also possible to provide desired properties by applying a surface treatment to an area that has a water-repellent property or an area that has a hydrophilic property by using a hydrophilic agent or a water-repellent agent depending on the property of the material. As the second sheet 6, any sheet may be used as long as it has a fiber layer. However, it is preferable that a non-woven fabric is used. There are various non-woven fabrics such as a spun lace non-woven fabric, a spun bond non-woven fabric, a melt-blown non-woven fabric, a needle punch non-woven fabric, an air-through non-woven fabric. Any one of them may be used as the second sheet 6. However, if a body fluid spot absorbent property is important, it is preferable to use an air-through non-woven fabric, and if a body fluid diffusion property is important, it is preferable to use a spun bond non-woven fabric.

In an example illustrated in FIG. 3, the second sheet 6 is made of a continuous single sheet that covers the both side slits 10, 10. Portions forming the concave grooves 11 on both sides are water-repellent regions 12 having water-repellent properties, and a portion between the water-repellent regions 12 is a hydrophilic region 13 having hydrophilic properties. Further in detail, it is preferable that all of the inner surfaces of the concave grooves 11 are water-repellent regions 12. In an example illustrated in the figure, the water-repellent regions 12 are formed in a range that includes all of the inner surfaces of the concave grooves 11 and includes portions extending from both sides of the concave grooves 11 with respect to the width direction of the sanitary napkin 1. It is preferable that the width of the water-repellent regions 12 formed in the second sheet 6 is 10 to 40 mm, preferably 15 to 30 mm. It is preferable that the relationship between the width of the water-repellent regions 12 formed in the second sheet 6 and the width of the slits 10 is "the slit width the width of the water-repellent regions 12".

In the case where the second sheet 6 is made of a continuous single sheet that covers the both side slits 10, 10, it is easy to transport the second sheet 6 and to align the second sheet 6 with other elements, and thus, handling of the second sheet 6 becomes easy in the manufacturing process of the sanitary napkin 1.

When the second sheet 6 is made of a single sheet, because the hydrophilic region 13 is formed between both sides of the water-repellent regions 12, the diffusion of the body fluids is suppressed in the water-repellent regions 12 on both sides, and the penetration (infiltration) of the body fluids that have been absorbed into the absorbent body 4 from the liquid permeable topsheet 3 is facilitated in the hydrophilic region 13 between the water-repellent regions 12. Therefore, an amount of the body fluids traveling on the front surface of the sanitary napkin 1 becomes smaller, the expelled (discharged) body fluids are quickly absorbed into the absorbent body 4 in a central region in the width direction, and the body fluids are diffused inside the absorbent body 4.

Regarding the second sheet 6, it is preferable that hydrophilic regions 13 are formed in portions that extend to outer side of the slits 10 in the width direction. With the above arrangement, even in the case where the body fluids, which have traveled on the body or the napkin surface, flow exceeding to outer side of the water-repellent regions 12 on both sides, the body fluids can be absorbed into the absorbent body 4 in the portions with the hydrophilic properties described above.

The water-repellent regions 12 may be provided at least in a range in which the concave grooves 11 are formed with respect to the longitudinal direction of the sanitary napkin 1. It is preferable that the water-repellent regions 12 are formed in a range longer than the above range in the napkin's longitudinal direction. Further, in the case where the second sheet 6 is provided covering almost the entire length of the sanitary napkin 1, the water-repellent regions 12 may be formed covering the entire length of the second sheet 6, or the water-repellent regions 12 may be formed in a longitudinal range that covers the slits 10, and further outer sides in the longitudinal direction may be hydrophilic regions 13. Further, in the case where the second sheet 6 is provided with a length that almost corresponds to the length of the slits 10 and covers the slits 10, it is preferable that the water-repellent regions 12 are formed extending to the entire length of the second sheet 6.

The water-repellent regions 12 of the second sheet 6 may be provided so as to prevent transition of the body fluids in the slits 10 from the inner side to the outer side in the width direction. As illustrated in FIG. 3, it is preferable that the water-repellent regions 12 of the second sheet 6 are formed in the entire inner surfaces of the concave grooves 11. By having the water-repellent properties in the entire inner surfaces of the concave groove 11, with the second sheet 6 having water-repellent properties, it becomes possible to reliably prevent the diffusion of the body fluids into the outer sides of the slits 10 in the width direction.

Figure 6:
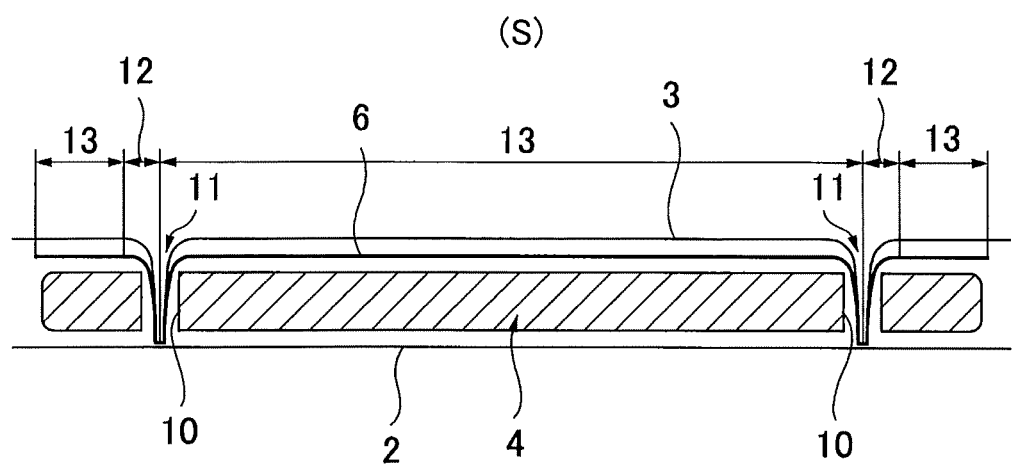
FIG. 6 is a cross-sectional view of a sanitary napkin according to a modified example.

FIG. 6 is a cross-sectional view of a sanitary napkin according to a modified example. As illustrated in FIG. 6, the water-repellent regions 12 of the second sheet 6 may be formed in a side surface of one of the inner side and the outer side of the concave grooves 11. In the case where only one of the side surfaces of the concave grooves 11 has water-repellent properties and the other side surface has hydrophilic properties, the body fluids, which has been diffused along the front surface side of the liquid permeable topsheet 3, are readily absorbed from the side surface having hydrophilic properties. Further, in the case where only one side surface of the concave grooves 11 has water-repellent properties, as illustrated in FIG. 6, it is preferable that only the outer side surface in the width direction has water-repellent properties. By causing the inner side surface in the width direction to be a portion of the second sheet 6 having hydrophilic properties or to be without second sheet 6, in the central region in the width direction, the range, in which the absorbent body surface has hydrophilic properties, is increased so that the wider range of the absorbent body can be used for absorbing the body fluids and the body fluid absorption efficiency is improved.

Next, structures, in which a predetermined region of the second sheet 6 is caused to have water-repellent properties, will be described. As illustrated in FIG. 2 and FIG. 3, in a first structure, a continuous sheet, which is made of a synthetic fiber non-woven fabric and covers the slits 10, 10 on both sides, may be used; no special process may be applied and the water-repellent properties owned by the water-repellent regions 12 may be used; and a hydrophilic agent may be applied to provide hydrophilic properties for the hydrophilic region 13. As the hydrophilic agent, by considering the safety of human body and the safety during the processes, a non-ionic active agent to which an ethylene oxide is added, an anionic active agent, or the like, may be preferably used as a single agent, or may be used as a mixture thereof. The ethylene oxide includes higher alcohols, higher fatty acid, alkyl phenol, etc., and the anionic active agent includes alkyl phosphate ester salt (octyl, dodecyl series), alkyl sulfate, etc. The amount of the hydrophilic agent to be applied to the sheet may vary according to the required performance. Normally, it is preferable that the amount of the hydrophilic agent is about 0.1 to 2.0 wt %, in particular, 0.2 to 1.0 wt % with respect to the dry weight of the target sheet.

Figure 7:
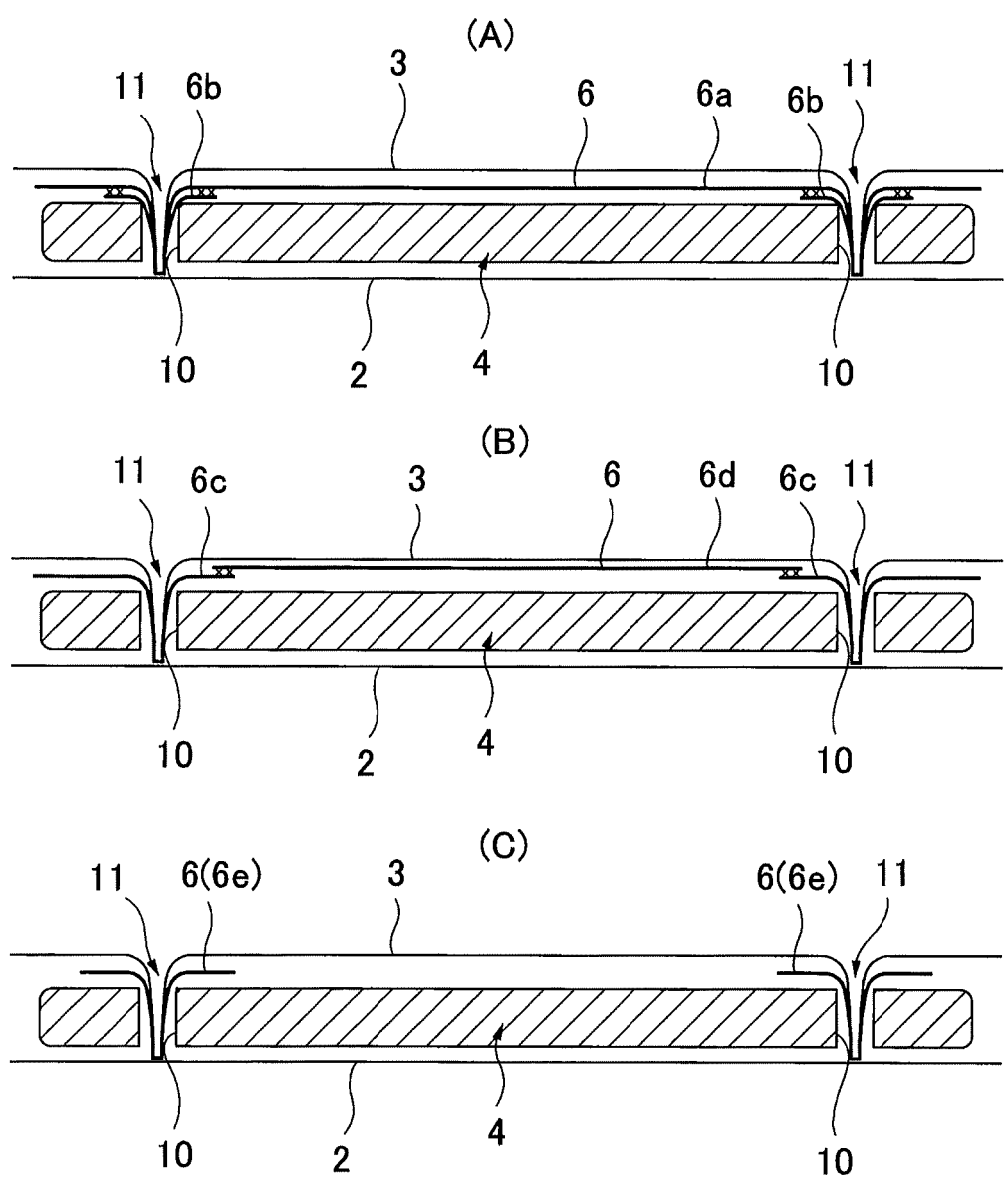
FIGS. 7(A) through 7(C) are cross-sectional views of sanitary napkins according to modified examples.

FIGS. 7(A) through (C) are cross-sectional views of sanitary napkins according to modified examples. In a second structure, in which a predetermined region of the second sheet 6 has water-repellent properties as illustrated in FIG. 7(A), the second sheet 6 may be made of: a continuous substrate sheet 6a that is made of a hydrophilic fiber and covers the slits 10, 10 on both sides; and a water-repellent sheet 6b that is joined to a water-repellent regions 12 of the substrate sheet 6a by joining means such as adhesive agent like a hot melt, a heat seal, and an ultrasonic sound wave seal. In this structure, it is possible to obtain desired properties without applying a special process by using the water-repellent properties and the hydrophilic properties owned by the materials.

In a third structure, in which a predetermined region of the second sheet 6 has water-repellent properties as illustrated in FIG. 7(B), the second sheet 6 may be made of: water-repellent sheets 6c, 6c that are provided at the slits 10, 10 on both sides; and a hydrophilic sheet 6d that is located between the water-repellent sheets 6c, 6c and is joined to the water-repellent sheets 6c, 6c by joining means such as adhesive agent like a hot melt, a heat seal, and an ultrasonic sound wave seal. As the water-repellent sheets 6c, 6c, a sheet made of a material having water-repellent properties or a sheet to which water-repelling treatment has been applied may be used. As the hydrophilic sheet 6d, a sheet made of a material having hydrophilic properties or a sheet to which hydrophilic treatment has been applied may be used.

In a fourth structure, in which a predetermined region of the second sheet 6 has water-repellent properties as illustrated in FIG. 7(C), the second sheet 6 may be made of two water-repellent sheets 6e, 6e, which are separated from each other and which covers the corresponding slits 10, 10 on both sides. As the water-repellent sheets 6e, a sheet made of a material having water-repellent properties or a sheet to which water-repelling treatment has been applied may be used. With the above arrangement, it is possible to reliably prevent diffusion of the body fluids to the outer side in the width direction at the slit portions, and, because the water-repellent sheets 6e, 6e are separated from each other and there is no second sheet 6 between them, the body fluid transition from the liquid permeable topsheet 3 to the absorbent body 4 is performed smoothly.

Figure 8:
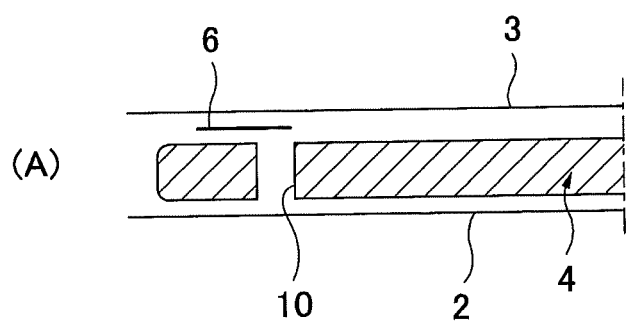
FIGS. 8(A) and 8(B) are cross-sectional views of a sanitary napkin illustrating (A) before compression, and (B) after compression.
Figure 8:
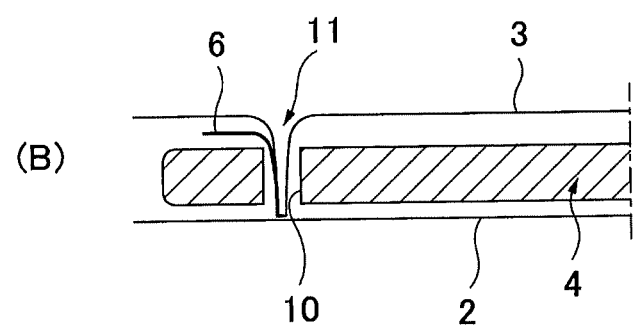

FIGS. 8(A) and 8(B) are cross-sectional views of a sanitary napkin illustrating (A) before compression, and (B) after compression. As the second sheet 6 with the fourth structure, as illustrated in FIGS. 8(A) and 8(B), the second sheet 6 may be provided so as to cover only side surfaces of outer sides of the slits 10 in the width direction. In a process for the above structure, as illustrated in FIG. 8(A), a second sheet 6 having water-repellent properties is provided on a surface above the slit 10 shifted toward an outer side in the width direction. Next, as illustrated in FIG. 8(B), a position of the second sheet 6 closer to the inner side in the width direction is compressed so that the side surface of the outer side of the slits 10 in the width direction is covered by an inner side portion of the second sheet 6 in the width direction.

It should be noted that, regarding the second sheet 6 used in an embodiment of the present invention, it is preferable that the thickness is 0.5 to 10 mm, preferably 1 to 7 mm, further preferably 1.5 to 4 mm in order to cause the sanitary napkin 1 to be relatively bulky compared with normal sanitary napkins. By causing the second sheet 6 to be relatively bulky, the body fluids readily penetrate in the second sheet 6, the expelled (discharged) body fluids are quickly absorbed into the absorbent body 4 in the central portion in the width direction, and it becomes possible to reduce the body fluids that travel on the surface. Further, by causing the thickness of the second sheet 6 to be thicker, the ratio of the second sheet 6 that occupies inside of the slits 10 when the concave grooves 11 are formed becomes greater, it becomes easy to maintain a state in which the slits 10 are open, and twists of the slits 10 are not readily generated. Further, cushioning properties of non-woven fabrics are higher than those of the absorbent body. Therefore, the rigidity of the slit portions becomes lower in a state in which the ratio of the second sheet 6 in the slits 10 is greater than in a state in which openings of the slits 10 are closed and both sides of absorbent bodies are close to each other, and thus, it becomes easy to follow body movements and the wearing comfort is increased. The thickness of the second sheet 6 is a value measured by a handy compression tester (KES-G5) manufactured by KATO TECH CO., LTD in the case where the pressure between press surfaces is 0.1 kPa. Further, it is preferable that a perforated film, in which body fluids readily penetrate, is used as the liquid permeable topsheet 3 because expelled body fluids are quickly absorbed. The fineness of a fabric, of which the second sheet 6 is made, is 2.2 to 6.7 dtex, preferably 3.3 to 5.6 dtex. Further, it is preferable that the weight per unit area of the second sheet 6 is 18 to 60 g/m$^2$, preferably 25 to 40 g/m$^2$.

Figure 9:
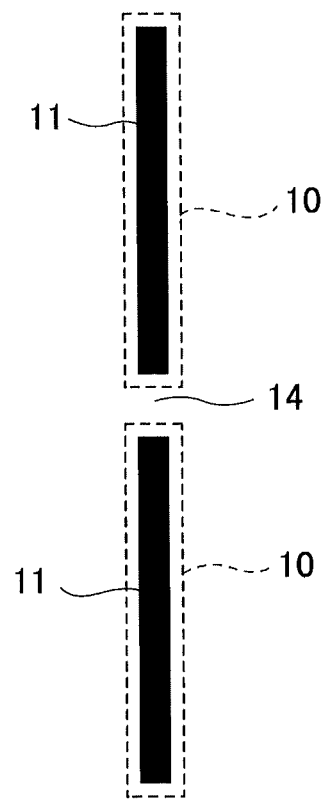
FIG. 9 is a planar view of a concave groove according to a modified example.

As illustrated in FIG. 1, the slits 10 may be formed continuously in a predetermined range in the longitudinal direction along the longitudinal direction in the sanitary napkin 1. Further, FIG. 9 is a planar view of a concave groove 11 according to a modified example. As illustrated in FIG. 9, the slits 10 may be formed discontinuously by forming one or more discontinuous portions 14 of the slits at intermediate positions in the longitudinal direction. In the case where the slits 10 are formed continuously, although it is possible to prevent the diffusion of the body fluids towards outer sides in the width direction continuously in the napkin's longitudinal direction, the absorbent body is separated in a long range in the napkin's longitudinal direction and there is a risk that the openings of the slits 10 are readily closed in the case where the leg pressure going from both sides to the inner sides in the width direction when being worn. On the other hand, in the case where the slits 10 are formed discontinuously, the discontinuous portions 14 provide reinforcement and it is possible to prevent the openings of the slits 10 from being closed. In the case where the slits 10 are discontinuous, it is preferable that the concave grooves 11 are also formed discontinuously by being separated by the discontinuous portions 14. Because the discontinuous portions 14 serve as paths for the body fluids, it is preferable to avoid providing the discontinuous portions 14 at least at the body fluid expelling portion and the vicinity thereof. It is preferable to provide the discontinuous portions 14 by having separations of 5 mm to 15 mm with respect to the longitudinal direction of the sanitary napkin 1. When the separation is less than 5 mm, effects of blocking the body fluids are reduced, and when the separation is greater than 15 mm, effects of slit enforcement are reduced.

OTHER EMBODIMENT EXAMPLES

Although the inner side of the side non-woven fabric sheet 7 is adhered to the liquid permeable topsheet 3 in an embodiment described above, the inner side of the side non-woven fabric sheet 7 may be doubly bent, and inside the doubly bent sheet, one or more threadlike elastic stretchable members, whose both ends or appropriate positions in the longitudinal direction are fixed to the intermediate positions of the sheet in the height direction, may be provided, and standing gathers, in which the doubly bent sheet portions stand towards the skin side due to the contractile force of the elastic stretchable members, may be formed.

As described above, preferable embodiments according to the present invention have been described. The present invention is not limited to the specific embodiments described above, and various modifications and variations may be possible within the range of the subject matter of the present invention recited in the claims.

Preferable aspects of the present invention will be appended below.

APPENDIX 1

An absorbent article is provided in which an absorbent body is provided between a liquid permeable topsheet and a backsheet, and a second sheet is provided between the liquid permeable topsheet and the absorbent body. Slits that penetrate in the thickness direction are formed along a longitudinal direction on both sides of the absorbent body in the width direction, a body-fluid-expelling-portion corresponding region is included between the slits, the second sheet is provided along the inner surface of the slits, and concave grooves, in which the second sheet and the backsheet are integrated, are formed in the slits. In the second sheet, at least a portion included in one of the side surfaces of the concave grooves has water-repellent properties.

With the arrangement described above, slits that penetrate in the thickness direction are formed along the longitudinal direction on both sides of the absorbent body in the width direction, the body-fluid-expelling-portion corresponding region is included between the slits, the second sheet is provided along the inner surface of the slits, and concave grooves, in which the second sheet and the backsheet are integrated, are formed in the slits. Here, because, at least a portion included in one of the side surfaces of the concave grooves has water-repellent properties in the second sheet, the body fluids, which are diffused inside the absorbent body, are blocked by the second sheet having water-repellent properties at the slits, and the body fluids are prevented from being diffused to the outer sides of the slits in the width direction. Therefore, it is possible to reliably prevent the lateral leakage of the body fluids, and it is possible to prevent a wearer from being visually concerned about the lateral leakage because there remains a portion of the absorbent body in a pure white state in which no body fluid is diffused in the outer side of the concave grooves in the width direction when the wearer checks a diffusion state of the body fluids after use.

Further, in the concave grooves, because the second sheet and the backsheet are integrated at the slits, the joined portion between the second sheet and the backsheet does not readily come off even if twists of the absorbent article are generated when it is worn, and thus, it is possible to increase the wearing comfort, and to maintain the leakage preventing effects.

APPENDIX 2

As an invention according to appendix 2, an absorbent article described in appendix 1 is provided, wherein, in the second sheet, portions, which are formed on the entire inner surface of the concave grooves, have water-repellent properties.

In an invention according to appendix 2, because the second sheet, which is formed on the entire inner surface of the concave grooves, has water-repellent properties, the inner side and the outer side of the concave grooves are formed by the portions having water-repellent properties, and thus, it is possible to further reliably prevent the body fluids from being diffused to the outer side in the width direction.

APPENDIX 3

As an invention according to appendix 3, an absorbent article described in appendix 1 or appendix 2 is provided, wherein, the second sheet is made of a continuous sheet that covers the slits on both sides, portions included in the concave grooves on both sides have water-repellent properties, and a portion between the water-repellent portions has hydrophilic properties.

In an invention according to appendix 3, the body fluid diffusion is suppressed by the portions on both sides that have water-repellent properties, and the penetration of the body fluids that have been absorbed into the absorbent body is facilitated at the portion having hydrophilic properties between the water-repellent portions. Further, because the second sheet is made of a single sheet, handling of the second sheet becomes easy in the manufacturing process of the absorbent article. In the case where a non-woven fabric made of synthetic fiber is used as the second sheet in this example, the portions having water-repellent properties may be formed by using the water-repellent properties of the material, and the portion having hydrophilic properties may be formed by applying a hydrophilic treatment such as applying a hydrophilic agent.

APPENDIX 4

As an invention according to appendix 4, an absorbent article described in appendix 1 or appendix 2 is provided, wherein, the second sheet is a joined sheet in which water-repellent sheets, which have been provided at the slits on both sides, and a hydrophilic sheet, which has been provided between the water-repellent sheets, are integrally joined to each other.

In an invention according to appendix 4, because the second sheet is made of a joined sheet in which water-repellent sheets, which have been provided at the slits on both sides, and a hydrophilic sheet, which has been provided between the water-repellent sheets, are integrally joined to each other, it is possible to use the material that has water-repellent properties or hydrophilic properties according to the portions, and thus, it is possible to easily form a water-repellent region and a hydrophilic region.

APPENDIX 5

As an invention according to appendix 5, an absorbent article described in appendix 1 or appendix 2 is provided, wherein, the second sheet consists of (is made of) water-repellent sheets that are provided at slits on both sides.

In an invention according to appendix 5, because the second sheet is made of water-repellent sheets that are provided at the slits on both sides, it is possible to reliably prevent the body fluids from being diffused to the outer sides of the slit portions in the width direction and it is possible to smoothly perform transition of the body fluids from the liquid permeable topsheet to the absorbent body because the water-repellent sheets on both sides are separated.

APPENDIX 6

As an invention according to appendix 6, an absorbent article described in any one of appendix 1 through appendix 5 is provided, wherein, the second sheet has hydrophilic properties at portions that extend beyond the slits towards the outer side in the width direction.

In an invention according to appendix 6, because the second sheet has hydrophilic properties at portions that extend beyond the slits towards the outer side in the width direction, even in the case where the body fluids flow exceeding the portions having water-repellent properties on both sides towards the outer sides in the width direction, it is possible to cause the body fluids to transition into the absorbent body at the portions having hydrophilic properties.

APPENDIX 7

As an invention according to appendix 7, an absorbent article described in any one of appendix 1 through appendix 6 is provided, wherein the liquid permeable topsheet and the second sheet are provided along the inner surface of the slits in the concave grooves, and the liquid permeable topsheet, the second sheet, and the back sheet are integrated in the slits.

In an invention according to appendix 7, because the liquid permeable topsheet and the second sheet are provided along the inner surface of the slits in the concave grooves, and, in the slits, the liquid permeable topsheet, the second sheet, and the back sheet are integrated by applying embossing from the front surface side of the liquid permeable topsheet, the concave grooves are formed on both sides of the skin contact surface of the absorbent article, and, due to the concave grooves, the body fluids flowing on the surface of the absorbent article towards the outer sides in the width direction are blocked, and it is possible to reliably prevent the lateral leakage of the body fluids.

APPENDIX 8

As an invention according to appendix 8, an absorbent article described in any one of appendix 1 through appendix 7 is provided, wherein, the thickness of the second sheet is 0.5 to 10 mm.

In an invention according to appendix 8, because the second sheet is relatively bulky by having the thickness of the second sheet 0.5 to 10 mm, the body fluids are readily penetrated in the second sheet and are quickly absorbed into the absorbent body, and thus, occurrences of lateral leakage due to the body fluids flowing on the surface are reduced.

APPENDIX 9

As an invention according to appendix 9, an absorbent article described in any one of appendix 1 through appendix 8 is provided, wherein, the slits are continuously formed along the longitudinal direction or discontinuously formed by having discontinuous portions at intermediate positions in the longitudinal direction.

In an invention according to appendix 9, the slits may be continuously formed along the longitudinal direction or may be discontinuously formed by having discontinuous portions at intermediate positions in the longitudinal direction. By having the slits formed discontinuously, it is possible to prevent the slits from readily collapsing when leg pressures are applied from the outer side to the inner side in the width direction when being worn.

The present application is based on and claims the benefit of priority of Japanese Priority Application No. 2016-040807 filed on Mar. 3, 2016, the entire contents of which are hereby incorporated herein by reference.

DESCRIPTION OF THE REFERENCE NUMERALS 1 sanitary napkin
2 liquid impermeable backsheet
3 liquid permeable topsheet
4 absorbent body
6 second sheet
7 side non-woven fabric sheet
10 slit
11 concave groove

What is claimed is:

1. An absorbent article comprising:
a liquid permeable topsheet;
a backsheet;
an absorbent body provided between the liquid permeable topsheet and the backsheet; and
a second sheet provided between the liquid permeable topsheet and the absorbent body, wherein
the absorbent article has slits that penetrate in the thickness direction thereof, the slits being respectively formed on both side portions of the absorbent body along a longitudinal direction thereof,
the absorbent body includes a body-fluid-expelling-portion corresponding region, the body-fluid-expelling-portion corresponding region being included between the slits,
the second sheet is provided along an inner surface of the slits,
the second sheet is folded back at the backsheet within the slits such that respective recesses are provided within the slits, and
the second sheet is patterned to include two first sheet portions and a second sheet portion, the first sheet portions defining the respective recesses provided by folding back the second sheet, each first sheet portion having water-repellent properties, the second sheet portion being continuously located between the first sheet portions and being interposed between the liquid permeable topsheet and the absorbent body, and the second sheet portion having hydrophilic properties.

2. The absorbent article according to claim 1, wherein the second sheet is a joined sheet in which water-repellent sheets, which are provided at the respective slits, and a hydrophilic sheet, which is provided between the water-repellent sheets, are integrally joined to each other.

3. The absorbent article according to claim 1, wherein the second sheet consists of water-repellent sheets that are provided at the respective slits.

4. The absorbent article according to claim 1, wherein portions of the second sheet that extend outside the slits in the width direction of the absorbent article have water-repellent properties.

5. The absorbent article according to claim 1, wherein the liquid permeable topsheet and the second sheet are provided along each of inner surfaces of the slits within the recesses, and, the liquid permeable topsheet, the second sheet, and the back sheet are integrated within the slits.

6. The absorbent article according to claim 1, wherein the thickness of the second sheet is 0.5 to 10 mm.

7. The absorbent article according to claim 1, wherein each slit is continuously formed along the longitudinal direction, or is discontinuously formed to include one or more discontinuous portions at intermediate positions in the longitudinal direction.

* * * * *